United States Patent
Hegde et al.

(10) Patent No.: US 6,911,472 B2
(45) Date of Patent: Jun. 28, 2005

(54) PHARMACEUTICAL COMPOSITION COMPRISING A HMG-COA REDUCTASE INHIBITOR

(75) Inventors: Deepak Hegde, Thane (IN); Sushrut Kulkarni, Kalyan (IN)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/476,816

(22) PCT Filed: May 3, 2002

(86) PCT No.: PCT/EP02/04891

§ 371 (c)(1),
(2), (4) Date: Apr. 13, 2004

(87) PCT Pub. No.: WO02/089788

PCT Pub. Date: Nov. 14, 2002

(65) Prior Publication Data

US 2004/0167085 A1 Aug. 26, 2004

(30) Foreign Application Priority Data

May 4, 2001 (GB) .............................. 0111077

(51) Int. Cl.⁷ ................. A61K 31/44; A61K 31/40; A61K 31/35; A61K 31/225
(52) U.S. Cl. .............. 514/548; 514/345; 514/419; 514/423; 514/460

(58) Field of Search ................. 514/345, 419, 514/423, 460, 548

(56) References Cited

U.S. PATENT DOCUMENTS

| | | | | |
|---|---|---|---|---|
| 5,030,447 A | * | 7/1991 | Joshi et al. ................. | 514/510 |
| 5,356,896 A | * | 10/1994 | Kabadi et al. .............. | 514/256 |
| 6,551,617 B1 | * | 4/2003 | Corbo et al. ................ | 424/465 |
| 6,680,341 B1 | * | 1/2004 | Kerc .......................... | 514/547 |

FOREIGN PATENT DOCUMENTS

| | | |
|---|---|---|
| EP | 0 547 000 | 6/1982 |
| WO | 94/16693 | 8/1994 |
| WO | 00/35425 | 6/2000 |
| WO | 01/93860 | 12/2001 |

OTHER PUBLICATIONS

The American Heritage Dictionary, Second College Edition, published 1982 by Houghton Mifflin Co., p. 805 "mix".*
* Kibbe Ah: "Handbook of Pharmaceutical Excipients", American Pharmaceutical Association, Washington, DC, USA, pp. 332–333 (2000).

* cited by examiner

*Primary Examiner*—Raymond J. Henley, III
(74) *Attorney, Agent, or Firm*—John D. Thallemer

(57) ABSTRACT

A pharmaceutical composition comprising as an active ingredient an HMG-CoA reductase inhibitor and an aminosugar.

12 Claims, No Drawings

PHARMACEUTICAL COMPOSITION COMPRISING A HMG-COA REDUCTASE INHIBITOR

The present invention relates to pharmaceutical compositions, comprising a HMG-CoA reductase inhibitor as an active ingredient.

Plasma cholesterol levels have been positively correlated with the incidence of clinical events associated with coronary heart disease (CHD). Thus, pharmacological interventions that reduce cholesterol levels in mammals may have a beneficial effect on CHD. In particular, decreased plasma low density lipoprotein (LDL) cholesterol levels are associated with decreased atherosclerosis and a decreased risk of CHD, and hypolipidemic agents used in either monotherapy or combination therapy are effective at reducing plasma LDL cholesterol levels and the subsequent risk of CHD.

Cholesterol metabolism in mammals involves a series of pathways including cholesterol absorption in the small intestine, cholesterol biosynthesis in numerous tissues (primarily the liver and small intestine), bile acid biosynthesis in the liver and reabsorption in the small intestine, synthesis of cholesterol-containing plasma lipoproteins by the liver and intestine, catabolism of the cholesterol-containing plasma lipoproteins by the liver and extrahepatic tissues and secretion of cholesterol and bile acids by the liver.

Cholesterol synthesis occurs in multiple tissues, but principally in the liver and the intestine. It is a multistep process starting from acetyl-coenzyme A catalyzed by a series of enzymes including hydroxymethylglutaryl-coenzyme A (HMG-CoA) reductase, HMG-CoA synthase, squalene synthetase, squalene epoxidase, squalene cyclase and lanosterol demethylase. Inhibition of catalysis of these enzymes or blocking HMG-CoA reductase gene expression is recognized as an effective means to reduce cholesterol biosynthesis ad can lead to a reduction in cholesterol levels. Known HMG-CoA reductase inhibitors include statins, such as lovastatin, simvastatin, pravastatin, fluvastatin, atorvastatin, mevastatin, rivastatin (cer(i)vastatin), pitavastatin (nisvastatin, itavastatin), rosuvastatin (visastatin), e.g. useful for the treatment of hypercholesterolemia.

HMG-CoA reductase inhibitors, such as statins however, may be instable in acidic environment, e.g. as described for pravastatin, for example in U.S. Pat. No. 5,030,447. To improve stability, in U.S. Pat. No. 5,030,447 it is suggested that pravastatin compositions should comprise one or more basifying agents to impart a desired pH of at least 9 to an aqueous dispersion of said composition, e.g. a composition comprising beside pravastatin one or more pharmaceutical excipients, such as fillers, binders, disintegrants, lubricants. Although stability of HMG-CoA reductase inhibitors, such as statins, may be improved by combination of a basifying agent with a HMG-CoA reductase inhibitor-, such as statin-, -composition, a local alkaline environment created after dissolution of tablets in the stomach may have negative impact on gastric mucosa which may become a prominent problem e.g. in case of long time therapy.

We have now found a pharmaceutical composition comprising an HMG-CoA reductase inhibitor which is stable and which may have less negative impact on gastric mucosa than pharmaceutical compositions of prior art.

In one aspect the present invention provides a pharmaceutical composition comprising as an active ingredient a HMG-CoA reductase inhibitor; characterised in that said pharmaceutical composition comprises an amino sugar; e.g. as a pH adjusting (basifying) agent, e.g. and characterised in that an aqueous dispersion of said composition has a pH of at least 7.0, preferably at least 8.0; e.g. in case of pravastatin as a HMG-CoA reductase inhibitor a pH of 7.0 to 8.7, preferably 8.0 to 8.7, e.g. and wherein the HMG-CoA reductase inhibitor is stable, with the proviso that compositions comprising dehydroepiandrosterone (DHEA), a desquamating agent selected from retinoids, acylated salicylic acid derivatives or HMG-CoA reductase inhibitors, and sugar derivatives, and comprising germs for a koji-making raw material and monacolin K, are excluded.

A composition comprising dehydroepiandrosterone (DHEA) and a desquamating agent selected from retinoids, acylated salicylic acid derivatives or HMG-CoA reductase inhibitors and sugar derivatives, is described in WO0126619. Such compositions are described to be usable in the cosmetic industry. A composition comprising germs (which germs comprises glucosamine) for a koji-making raw material, such as wheat or rice germs, and monacolin K (lovastatin) is described in JP2000106834. In JP2000106834 it is also described, that such compositions may be obtained by heating a mixture of wheat germs and rice germs with water, inoculating the mixture with *Monascus pilosus* IFO4520, culturing for 4 to 8 days, heating to 110° C. for 20 minutes, drying the mixture obtained, e.g. to reduce the moisture content to 10% or less, and pulverizing.

According to the present invention a HMG-CoA reductase inhibitor includes, e.g. one or more, preferably one, HMG-CoA reductase inhibitor which is unstable in acidic environment, such as compounds as disclosed and cited in HMG-CoA reductase inhibitor patent filings, including statins. Such patent filings e.g. include U.S. Pat. No. 4,231,938 (including e.g. lovastatin); EP0033538 (including e.g. simvastatin); GB2077264 (including e.g. pravastatin); EP0114027 (including e.g. fluvastatin); EP0247633 (including e.g. atorvastatin); U.S. Pat. No. 3,983,140 (including e.g. mevastatin); EP0491226 (including e.g. rivastatin; cer(i)vastatin); U.S. Pat. No. 5,011,930 (including e.g. pitavastatin, Nissan/Sankyo's nisvastatin (NK-104) or itavastatin); U.S. Pat. No. 5,260,440 (including e.g. rosuvastatin or visastatin (ZD-4522) of Shionogi-Astra/Zeneca); and U.S. Pat. No. 5,753,675 (including statins related to statins as described above); the content of said cited patent filings being introduced herein by reference. Preferably a HMG-CoA reductase Inhibitor is selected from statins, such as lovastatin, simvastatin, pravastatin, fluvastatin, atorvastatin, mevastatin, rivastatin (cer(i)vastatin), pitavastatin (nisvastatin, itavastatin), rosuvastatin (visastatin) or a related statin compound; more preferably from the group consisting of lovastatin, simvastatin, pravastatin, fluvastatin, atorvastatin, mevastatin, rivastatin (cer(i)vastatin), pitavastatin (nisvastatin, itavastatin) and rosuvastatin (visastatin), still more preferably pravastatin.

In another aspect the present invention provides a pharmaceutical composition according to the present invention comprising as an active ingredient a statin, e.g. at least one, such as a statin selected from the group consisting of lovastatin, simvastatin, pravastatin, fluvastatin, atorvastatin, mevastatin, rivastatin (cer(i)vastatin), pitavastatin (nisvastatin, itavastatin) or rosuvastatin (visastatin), more preferably pravastatin.

A pharmaceutical composition according to the present invention may be obtained by mixing an HMG-CoA reductase inhibitor with an aminosugar. Preferably said aminosugar is an aminosugar which is able to adjust a pH of at least 7.0 of said composition in aqueous dispersion. Preferably said aminosugar is used as a pH-adjusting (basifying) agent. A preferred aminosugar according to the present present invention includes N-methylglucamine.

The necessary amount of the aminosugar in respect with the amount of the HMG-CoA reductase inhibitor to obtain a pH of at least 7.0 in an aqueous dispersion may be critical and may be found by pre-testing. In case of N-methylglucamine as an aminosugar and in case of pravastatin as the HMG-CoA reductase inhibitor preferably the amount of the aminosugar in respect with the amount of the HMG-CoA reductase inhibitor is 15% per weight and less, e.g. 6% to 15%.

A pharmaceutical composition according to the present invention may comprise beside the active ingredient and an aminosugar pharmaceutically acceptable excipient, e.g. one or more, such as excipient which is useful in the production of pharmaceutical compositions. Appropriate excipient may be found by pre-testing. Examples of such excipient include, e.g. one or more, filler and/or binder and/or disintegrant and/or lubricant, such as celluloses, e.g. including
  powdered cellulose, e.g. as a filler;
  microcrystalline cellulose, such as Avicel, e.g. including Avicel 102®; e.g. as a filler;
  carboxymethylcelluloses, e.g. including croscarmellose sodium (crosslinked Na-carboxymethylcellulose), e.g. as a disintegrant;
  hydroxyalkylcelluloses, e.g. including hydroxypropylcellulose, e.g. as a binder;
starches, e.g. including wheat starch, e.g. as a filler or as a binder;
polyvinylpyrrolidones, e.g. as a binder, e.g. including cross linked polyvinylpyrrolidones,
silicium (silicon) dioxides, e.g. including $SiO_2$ colloidal, e.g. as a disintegrant;
acrylic and methycrylic polymers, e.g. homo- and copolymers, such as the potassium salt of a low crosslinked carboxylic cation-exchange resin prepared from methacrylic acid and divinylbenzene, e.g. polyacrilin potassium, e.g. as a disintegrant;
lactose, e.g. as a filler;
Mg-stearate, Ca-stearate, e.g. as a lubricant;
Ca-sulphate, e.g. as a filler;
$CAHPO_4$, also known as calcium phosphate or dicalcium phosphate, e.g. as a filler,
MgAl-silicate, e.g. as a disintegrant.

In another aspect the present invention provides a pharmaceutical composition according to the present invention and further comprising pharmaceutically acceptable excipient, e.g. comprising, e.g. selected from the group consisting of, one or more filler, and/or binder and/or disintegrant and/or lubricant, e.g.
a pharmaceutical composition consisting of
  a HMG-CoA reductase inhibitor as an active ingredient,
  an aminosugar, and
  pharmaceutically acceptable excipient selected from the group consisting of one or more filler and/or binder and/or disintegrant and/or lubricant.

In a preferred embodiment of the present invention the pharmaceutical composition beside an HMG-CoA reductase inhibitor and an aminosugar further comprises one or more filler, binder, disintegrant and lubricant.

A pharmaceutical composition according to the present invention may be in any form, e.g. in solid form or in a liquid form, e.g. in the form of a suspension or emulsion for oral administration.

In another aspect the present invention provides a pharmaceutical composition according to the present invention which is in solid form.

Solid forms e.g. include granules, powders, tablets, preferably tablets. A solid form according to the present invention preferably include solid forms for oral administration.

In another aspect the present invention provides a pharmaceutical composition according to the present invention which is in in the form of a tablet, e.g. for oral administration.

A tablet according to the present invention includes a non-dispersible and a dispersible tablet. A dispersible tablet is understood to include a tablet which forms a (homogenous) dispersion in aqueous solvent, e.g. resulting in an emulsion or suspension for oral administration. A preferred HMG-CoA reductase inhibitor includes pravastatin, e.g. in the form of a sodium salt.

A tablet according to the present invention includes a tablet wherein the amount of the aminosugar is 5.0% and less of the total tablet weight, e.g. 2.0% and less, such as 0.5% to 5.0% and wherein the HMG-CoA reductase inhibitor is pravastatin, e.g. in the form of a sodium salt.

In a preferred embodiment of the present invention a pharmaceutical composition according to the present invention which is In the form of a tablet, e.g. for oral administration, may be prepared as follows:

An HMG-CoA reductase inhibitor, such as a statin, e.g. pravastatin, such as pravastatin in the form of a sodium salt, may be mixed with filler and/or binder. The mixture obtained may be granulated with water. Alternatively the HMG-CoA reductase inhibitor may be mixed with filler and/or binder and the mixture obtained may be granulated with water in which one or more, preferably one, aminosugar as a pH-adjusting (basifying) agent, is dissolved. Granulate obtained may be dried and optionally processed through a sieve, preferably a sieve having a pore seize between 1.0 to 3.0 mm, such as 2.0 mm. Granulate obtained may be optionally mixed with further aminosugar as a pH-adjusting (basifying) agent, in the case that during granulation aminosugar was already present, and in the case that during granulation no aminosugar was present, granulate obtained is mixed with aminosugar as a pH-adjusting (basifying) agent. A mixture obtained may be compressed to obtain tablets.

Preferred dosage units include such which are normally useful, e.g. which are known to be useful, for a specific HMG-CoA reductase inhibitor. In the case that pravastatin sodium is used as a HMG-CoA reductase inhibitor most preferably one tablet contains 10, 20 or 40 mg of pravastatin sodium.

In another aspect the present invention provides a tablet for oral administration according to the present invention comprising, e.g. consisting of, pravastatin in the form of a sodium salt, and further comprising filler and/or binder and/or disintegrant and/or lubricant; and aminosugar; e.g. as a pH adjusting (basifying) agent, in such an amount, that a dispersion of said tablet in water has a pH of 7.0 to 8.7, preferably of 8.0 to 8.7.

In another aspect the present invention provides a tablet for oral administration comprising, e.g. consisting of, pravastatin in the form of a sodium salt, filler, binder, disintegrant, lubricant and aminosugar; e.g. as a pH adjusting (basifying) agent, in such an amount, that a dispersion of said tablet in water has a pH of 7.0 to 8.7, preferably of 8.0 to 8.7.

In another aspect the present invention provides a tablet according to the present invention, comprising, e.g. consisting of
pravastatin in the form of a sodium salt as an active ingredient, and
   lactose, microcristalline cellulose, polyvinylpyrrolidone, croscarmellose sodium, and Mg-stearate, or
   dicalcium hydrogen phosphate, powdered cellulose, hydroxypropylcellulose, $SiO_2$, Ca-stearate and the potassium salt of a low crosslinked carboxylic cation-exchange resin prepared from methacrylic acid and divinylbenzene, or
   dicalcium hydrogen phosphate, powdered cellulose, wheat starch, $SiO_2$, Ca-stearate and the potassium salt of a low crosslinked carboxylic cation-exchange resin prepared from methacrylic acid and divinylbenzene,
and
N-Methyl glucamine as a pH-adjusting (basifying) agent in such an amount, that a dispersion of said tablet in water has a pH of 7.0 to 8.7.

In another aspect the present invention provides a process of the production of a tablet for oral administration comprising as an active ingredient an HMG-CoA reductase inhibitor, which process comprises the steps
a. mixing an HMG-CoA reductase inhibitor with filler and/or binder, e.g. with filler and binder,
b. granulating the mixture obtained in step a., e.g. with water as a granulation liquid, or with water wherein aminosugar is dissolved, e.g. in an amount, that a dispersion of a tablet for oral administration obtained in step f. in water has a pH of at least 7.0; or has a pH of below 7.0, to obtain a granulate, e.g. granulated particles containing an HMG-CoA reductase inhibitor and filler and/or binder, and optionally aminosugar,
c. drying a granulate obtained in step b.,
d. optionally processing a granulate obtained in step c. through a sieve,
e. in case that no aminosugar was present in step b., mixing granulate obtained in step c. or step d. with aminosugar as a pH-adjusting (basifying) agent in such an amount, that a dispersion of said tablet for oral administration in water has a pH of at least 7.0, and, if aminosugar was present in step a., optionally mixing granulate obtained in step c. or step d. with aminosugar as a pH-adjusting (basifying) agent in such an amount, that a dispersion of said tablet for oral administration in water has a pH of at least 7.0, e.g. in the case that the amount of aminosugar present in step b. was not sufficient to adjust a pH of at least 7.0; and optionally, e.g. preferably, with disintegrant and/or lubricant, e.g. disintegrant and lubricant; and
f. compressing the mixture obtained in step e. to obtain tablets, e.g. useful for oral administration.

In the case that pravastatin sodium is used as an HMG-CoA reductase inhibitor preferably a tablet contains 10, 20 or 40 mg of pravastatin sodium, e.g. and a dispersion of said tablet for oral administration in water has a pH of 7.0 to 8.7, preferably 8.0 to 8.7.

In a dispersion in water of a compressed tablet according to the present invention the HMG-CoA reductase inhibitor may be stable under normal environment humidity conditions for 1 months and more.

EXAMPLES FOR THE PRODUCTION OF TABLETS

As an active ingredient pravastatin in the form of a sodium salt is used.

The active ingredient is mixed with filler(s) and binder(s) and the mixture obtained is granulated in a wet granulation process with water. The granulate obtained is dried and processed through a sieve having a pore seize of 2.0 mm. The granulated particles obtained are mixed with disintegrant(s), lubricant(s) and an aminosugar, or, alternatively, the active ingredient is mixed with filler(s) and binder(s) and the mixture obtained is granulated in a wet granulation process with water in which an aminosugar has been dissolved. The granulate obtained is dried and processed through a sieve having a pore seize of 2.0 mm. The granulated particles obtained are mixed with disintegrant(s) and lubricant(s).

The mixture obtained according to either process is compressed into tablets comprising 10, 20 or 40 mg of pravastatin in the form of a sodium salt.

Ingredients of 3 different tablet compositions obtained (in % per weight of one tablet) according to both procedures described above are as set out in TABLE 1 below:

TABLE 1

|  | Preparation 1 | Preparation 2 | Preparation 3 |
|---|---|---|---|
| Pravastatin in the form of a sodium salt | 10.00 | 10.00 | 10.00 |
| Lactose as a filler | 68.20 | — | — |
| Microcrystallline cellulose*) as a filler | 13.50 | — | — |
| Dicalcium hydrogen phosphate as a filler | — | 65.00 | 65.00 |
| Powdered cellulose as a filler | — | 17.00 | 17.00 |
| Polyvinylpyrrolidone as a binder | 0.50 | — | — |
| Hydroxypropylcellulose as a binder | — | 1.00 | — |
| Wheat starch as a binder | — | — | 1.00 |
| Croscarmellose sodium as a disintegrant | 6.00 |  |  |
| $SiO_2$ colloidal as a disintegrant | — | 2.50 | 2.50 |
| Polyacrilin***) potassium as a disintegrant | — | 2.50 | 2.50 |
| Mg-stearate as a lubricant | 1.00 | — | — |
| Ca-stearate as a lubricant | — | 1.00 | 1.00 |
| Meglumine**) as a pH adjusting agent | 0.80 | 1.00 | 1.00 |

*)Avicel pH 102
**)N-Methyl glucamine
***)Potassium salt of a low crosslinked carboxylic cation-exchange resin prepared from methacrylic acid and divinylbenzene.

The pH of an aqueous dispersion of a tablet obtained as described in that example and comprising the ingredients of a Preparation 1, Preparation 2 or Preparation 3 as set out in TABLE 1 above, is determined and is between 8.0 and 8.7. Preparation 1, Preparation 2 and Preparation 3 is stable for more than 1 month under normal environment humidity conditions.

What is claimed is:
1. A pharmaceutical composition comprising as an active ingredient an HMG-CoA reductase inhibitor; characterized in that said composition comprises an aminosugar, wherein said aminosugar is mixed and/or granulated with said HMG-CoA reductase inhibitor, with the proviso that compositions
   comprising dehydroepiandrosterone (DHEA), a desquamating agent selected from retinoids, acylated salicylic acid derivatives or HMG-CoA reductase inhibitors, and sugar derivatives, and
   comprising germs for a koji-making raw material and monacolin K, are excluded.
2. A pharmaceutical composition according to claim 1, further comprising pharmaceutically acceptable excipient.
3. A pharmaceutical composition according to claim 2, wherein pharmaceutically acceptable excipient is selected from the group comprising one or more filler and/or binder and/or disintegrant and/or lubricant.

4. A pharmaceutical composition of comprising
a HMG-CoA reductase inhibitor as an active ingredient,
an aminosugar, and
pharmaceutically acceptable excipient selected from one or more filler and/or binder and/or disintegrant and/or lubricant,
wherein said aminosugar is mixed and/or granulated with said HMG-CoA reductase inhibitor.

5. A pharmaceutical composition according to claim 2, wherein the pharmaceutically acceptable excipient comprises one or more filler, binder, disintegrant and lubricant.

6. A pharmaceutical composition according to claim 1, wherein the HMG-CoA reductase inhibitor is a statin.

7. A pharmaceutical composition according to claim 6, wherein the statin is selected from the group consisting of lovastatin, simvastatin, pravastatin, fluvastatin, atorvastatin, mevastatin, rivastatin (cer(i)vastatin), pitavastatin (nisvastatin, itavastatin) and rosuvastatin (visastatin).

8. A pharmaceutical composition according to claim 7, wherein the statin is pravastatin.

9. A pharmaceutical composition according to claim 1 which is in solid form.

10. A pharmaceutical composition according to claim 9 which is in the form of a tablet.

11. A tablet for oral administration consisting of pravastatin in the form of a sodium salt, one or more filler, binder, disintegrant and/or lubricant, and aminosugar as a pH-adjusting (basifying) agent in such an amount, that a dispersion of said tablet in water has a pH of 7.0 to 8.7.

12. A tablet according to claim 11 consisting of pravastatin in the form of a sodium salt as an active ingredient, and lactose, microcristalline cellulose, polyvinylpyrrolidone, croscarmellose sodium, and Mg-stearate, or dicalcium hydrogen phosphate, powdered cellulose, hydroxypropylcellulose, $SiO_2$, Ca-stearate and the potassium salt of a low crosslinked carboxylic cation-exchange resin prepared from methacrylic acid and divinylbenzene, or dicalcium hydrogen phosphate, powdered cellulose, wheat starch, $SiO_2$, Ca-stearate and the potassium salt of a low crosslinked carboxylic cation-exchange resin prepared from methacrylic acid and divinylbenzene, and N-Methyl glucamine as a pH-adjusting (basifying) agent in such an amount, that a dispersion of said tablet in water has a pH of 7.0 to 8.7.

\* \* \* \* \*